US012754154B2

(12) United States Patent
Karoum et al.

(10) Patent No.: US 12,754,154 B2
(45) Date of Patent: Oct. 6, 2026

(54) NMR CHARACTERIZATION OF MODIFIED DRILLING FLUIDS

(71) Applicant: Schlumberger Technology Corporation, Sugar Land, TX (US)

(72) Inventors: Reda Karoum, Houston, TX (US); Adam Colbourne, Cambridge (GB); Benjamin Merceron, Clamart (FR); Jerry Thomas Connaughton, Richmond, TX (US); Timothy Lesko, Rosenberg, TX (US); Brian Ligertwood, Houston, TX (US); Chemsseddine Bouguetta, Beijing (CN)

(73) Assignee: Schlumberger Technology Corporation, Sugar Land, TX (US)

( * ) Notice: Subject to any disclaimer, the term of this patent is extended or adjusted under 35 U.S.C. 154(b) by 156 days.

(21) Appl. No.: 18/851,167

(22) PCT Filed: May 16, 2023

(86) PCT No.: PCT/US2023/022374
§ 371 (c)(1),
(2) Date: Sep. 26, 2024

(87) PCT Pub. No.: WO2023/224988
PCT Pub. Date: Nov. 23, 2023

(65) Prior Publication Data

US 2025/0052705 A1 Feb. 13, 2025

Related U.S. Application Data

(60) Provisional application No. 63/364,849, filed on May 17, 2022.

(51) Int. Cl.
*G01V 3/00* (2006.01)
*G01N 1/44* (2006.01)
(Continued)

(52) U.S. Cl.
CPC ............ *G01N 24/082* (2013.01); *G01N 1/44* (2013.01); *G01N 33/2823* (2013.01); *G01N 33/2847* (2013.01); *G01R 33/50* (2013.01)

(58) Field of Classification Search
CPC .... G01N 24/082; G01N 1/44; G01N 33/2823; G01N 33/2847; G01R 33/50
(Continued)

(56) References Cited

U.S. PATENT DOCUMENTS 9,777,542 B2 10/2017 Stock et al.
10,257,566 B2 4/2019 Monk
(Continued)

FOREIGN PATENT DOCUMENTS

WO 2021081144 A1 4/2021

OTHER PUBLICATIONS

International Search Report and Written Opinion issued in International Patent application PCT/US2023/022374 on Sep. 4, 2023, 11 pages.

(Continued)

*Primary Examiner* — Walter L Lindsay, Jr.
*Assistant Examiner* — Frederick Wenderoth
(74) *Attorney, Agent, or Firm* — Jeffrey D. Frantz

(57) ABSTRACT

A method for evaluating a multiphase drilling fluid includes receiving a sample of the multiphase drilling fluid and modifying the sample to enhance a separation of a first NMR peak corresponding to a first fluid phase component and a second NMR peak corresponding to a second fluid phase component. A nuclear magnetic resonance (NMR) measurement is made of the modified sample and evaluated to compute a property of the drilling fluid.

26 Claims, 11 Drawing Sheets

(51) Int. Cl.
*G01N 24/08* (2006.01)
*G01N 33/28* (2006.01)
*G01R 33/50* (2006.01)

(58) Field of Classification Search
USPC .......................................................... 324/309
See application file for complete search history.

(56) References Cited

U.S. PATENT DOCUMENTS

| | | | | |
|---|---|---|---|---|
| 11,047,815 | B2 | 6/2021 | Reiderman | |
| 2006/0122779 | A1 | 6/2006 | Minh | |
| 2009/0289628 | A1 | 11/2009 | Cao Minh | |
| 2015/0192011 | A1 | 7/2015 | Mandal | |
| 2018/0003654 | A1* | 1/2018 | Chen .................... | G01R 33/307 |
| 2022/0050223 | A1 | 2/2022 | Tang et al. | |
| 2022/0178253 | A1 | 6/2022 | Karoum | |

OTHER PUBLICATIONS

Rismanto et al., Explorative study of NMR drilling fluid measurements, Annual transaction of the Nordic Rheology Society, vol. 15, 2007, 7 pages.

Zhang et al., Research on Oil-based drilling fluid droplet by low-field NMR, Applied Magnetic Resonance, vol. 47, (12), pp. 1339-1352, 2016. (DOI:10.1007/s00723-016-0845-x).

Saasen et al., Removal of magnetic metallic contamination—Improved drilling fluid performance, SPE-195721-MS, Paper presented at the SPE Offshore Europe Conference and Exhibition, Sep. 3-6, 2019, 9 pages.

Pattarini et al., Ditch magnet removal of steel particles, SPE-185939-MS, Paper presented at the SPE Bergen One Day Seminar, Bergen, Norway, Apr. 2017, 6 pages.

* cited by examiner

NMR CHARACTERIZATION OF MODIFIED DRILLING FLUIDS

CROSS REFERENCE TO RELATED APPLICATIONS

This application is a National Stage Entry of International Application No. PCT/US2023/022374, filed May 16, 2023, which claims the benefit of U.S. Provisional Application No. 63/364,849, entitled "NMR CHARACTERIZATION OF MODIFIED DRILLING FLUIDS," filed May 17, 2022, the disclosure of which is hereby incorporated herein by reference.

FIELD OF THE INVENTION

Disclosed embodiments relate generally to characterization and monitoring of drilling fluids and more particularly to nuclear magnetic resonance (NMR) methods for characterizing and monitoring drilling fluids.

BACKGROUND INFORMATION

When building a well for the production of hydrocarbons such as oil and gas, drilling fluid is often circulated through the well for a number of purposes. For example, drilling fluid is commonly intended to provide hydrostatic pressure to the formation, cool and lubricate the drill bit, flush cuttings away from the drill bit and carry them to the surface, and provide hydraulic power to various downhole tools.

Drilling fluids are often highly engineered to provide for the above uses. Common drilling fluids may be water-based, oil-based, or synthetic-based multiphase fluids and often include clay, polymer, chemical, and other additives to obtain a desired suite of fluid properties. During a drilling operation the drilling fluid is exposed to high temperatures and pressures. Moreover, formation fluids such as oil, gas, and water may mix with the drilling fluid changing its composition, properties, and operational performance. Fluid properties including water content, oil content, and solids content are commonly measured during a downhole operation to monitor these changes.

The use of nuclear magnetic resonance (NMR) in oilfield applications is well known, for example, to evaluate drilling fluid or formation core samples as well as to make downhole measurements in the wellbore. As described above, drilling fluids are often highly complex multi-phase fluids. One difficulty in evaluating drilling fluids with NMR is that the NMR response of the multiple phases commonly overlap (e.g., in T1 and/or T2 relaxation times). This overlapping response complicates subsequent analysis, for example, the calculation of an oil to water ratio of the fluid. There is a need in the art for improved NMR methods to address this difficulty.

SUMMARY

A method for evaluating a multiphase drilling fluid includes receiving a sample of the multiphase drilling fluid and modifying the sample to enhance a separation of a first NMR peak corresponding to a first fluid phase component and a second NMR peak corresponding to a second fluid phase component. A nuclear magnetic resonance (NMR) measurement is made of the modified sample and evaluated to compute a property of the drilling fluid.

This summary is provided to introduce a selection of concepts that are further described below in the detailed description. This summary is not intended to identify key or essential features of the claimed subject matter, nor is it intended to be used as an aid in limiting the scope of the claimed subject matter.

BRIEF DESCRIPTION OF THE DRAWINGS

For a more complete understanding of the disclosed subject matter, and advantages thereof, reference is now made to the following descriptions taken in conjunction with the accompanying drawings, in which.

DETAILED DESCRIPTION

Figure 1:
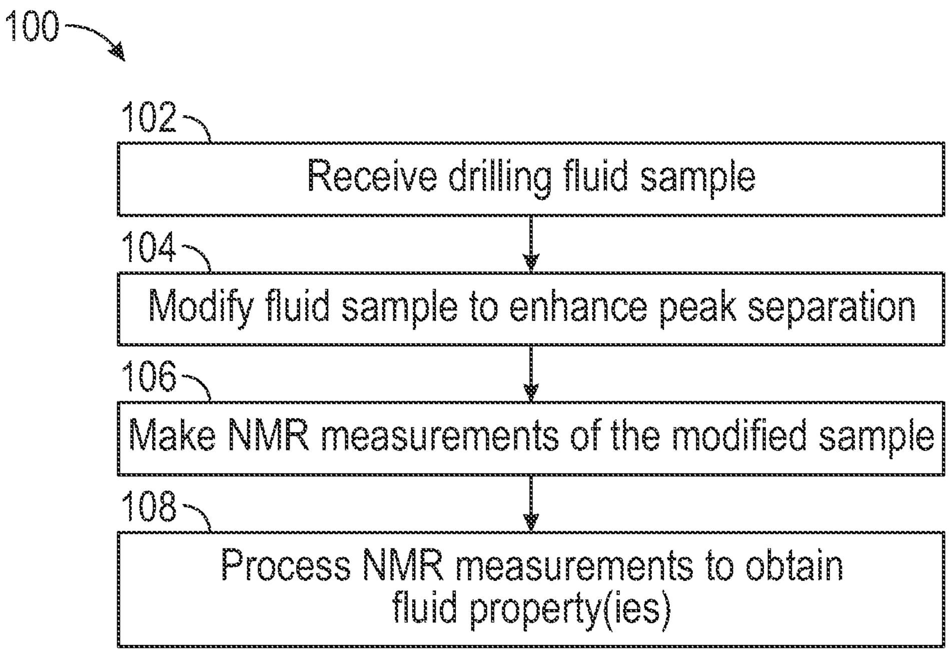
FIG. 1 depicts a flow chart of one disclosed method embodiment.

In a first embodiment, a method for evaluating a multiphase drilling fluid is disclosed. The method includes receiving a sample of the multiphase drilling fluid and modifying the sample to enhance a separation of a first NMR peak corresponding to a first fluid phase component (e.g., an oil phase) and a second NMR peak corresponding to a second fluid phase component (e.g., a water/brine phase). A nuclear magnetic resonance (NMR) measurement is made of the modified sample and evaluated to compute a property of the drilling fluid (e.g., an oil water ratio).

The disclosed embodiments may provide various technical advantages. For example, the disclosed methodology may provide for improved characterization of drilling fluids, for example, to characterize the oil water ratio of the fluid. Moreover, the disclosed embodiments may enable the NMR response of oil and water phases in the drilling fluid to be separated, thereby enabling the characterization of a wider range of fluids (e.g., enabling the NMR characterization of fluids that were previously difficult or even impossible to evaluate using NMR). In certain embodiments, the disclosed measurement method may be executed rapidly, thereby providing substantially real time measurements of drilling fluid properties (e.g., within a few minutes of receiving the sample).

In oilfield NMR measurements a static magnetic field (the $B_0$ field) is applied to a sample (e.g., via one or more permanent magnets in an NMR measurement tool). A radio frequency (RF) pulse sequence (the $B_1$ field) is applied to the sample and corresponding rotating magnetic fields stimulated in the sample are measured through the induction of an electrical signal in an antenna. Time constants T1 and T2 are commonly evaluated in NMR measurements from the received electrical signals (referred to herein as echoes). In general, the applied $B_0$ field causes the atoms in the sample to align along and rotate (precess) about the axis of the applied magnetic field. NMR measures the relaxation to equilibrium of this magnetization after applying a series of RF pulses to tip the magnetization in a direction orthogonal to the applied magnetic field. The spin-lattice relaxation time T1 (also referred to as the longitudinal polarization time) is the time constant for the longitudinal magnetization to return to its thermal equilibrium value in the static magnetic field. The spin-spin relaxation time T2 (also referred to as the transverse polarization time) is the time constant for the transverse magnetization to return to its thermal equilibrium value of zero.

One common pulse sequence used to measure the T2 relaxation time distribution is referred to as the Carr-Purcell-Meiboom-Gill (the CPMG) sequence. A CPMG sequence includes an initial idle time or wait time to allow fluid nuclei to come to equilibrium with the static ($B_0$) magnetic field. A series of RF pulses is then applied, initially stimulating a deviation from thermal equilibrium and then refocusing the effects of T1 relaxation to enable observation of T2 relaxation in isolation, with signal "echoes" recorded between adjacent refocusing pulses. The echo amplitude decays with time during the CPMG sequence. A T2 distribution may be determined from NMR measurements made using a single CPMG pulse sequence by fitting the echo amplitude (or amplitude decay) to an exponential model as is known to those of ordinary skill in the art.

NMR measurements that make use of a stack (or set) of CPMG pulse sequences separated by corresponding wait times (WTs) are commonly used to measure both T1 and T2 distributions. This set (or stack) of CPMG sequences is commonly referred to as a "inversion recovery" CPMG sequence and can be used to generate NMR signals (echoes) as expressed mathematically below:

$$S(WT, n, TE) = \int dT1 \cdot dT2 \cdot f(T1, T2) \cdot K(WT, n, TE, T1, T2)$$

where S(WT, $t_{echo}$) represents the echoes (i.e., the NMR signal), $$K(WT, n, TE, T1, T2) = M_0 \cdot \left(1 - \exp\left(-\frac{WT}{T1}\right)\right) \exp\left(-n\frac{TE}{T2}\right)$$

and where $M_0$ is a proportionality constant. The kernel function K( . . . ) describes spin dynamics of excited proton signals as a function of pulsing parameters, WT, n, and TE, as well as intrinsic fluid properties T1 and T2. One-dimensional distributions of the T1 and T2 relaxation times and/or a joint two-dimensional distribution of T1 and T2 may be obtained from NMR echoes (e.g., via a Laplacian or fast Laplacian inversion). These one-dimensional and two-dimensional distributions are referred to herein as NMR measurements. A joint probability distribution f (T1, T2) obtained via such measurements (and referred to herein as a T1T2 plot) presents distinctive signatures of complex fluids (e.g., in two dimensional plots of T1 versus T2 as described in more detail below).

FIG. 1 depicts a flow chart of one disclosed method embodiment 100 for evaluating drilling fluid. The method 100 includes obtaining (or receiving) a sample of the drilling fluid at 102, for example, from a drilling rig or some other drilling fluid source. The method 100 further includes modifying the drilling fluid sample. The sample modification is intended to enhance a peak separation between at least first and second peaks (or between a first group of peaks and a second group of peaks) in an NMR measurement (e.g., between a first peak related to an oil phase in the sample and second peak related to a water or brine phase in the sample). NMR measurements are made of the modified sample at 106 and processed at 108 to obtain at least one property of the drilling fluid (e.g., an oil water ratio of the fluid).

Figure 2:
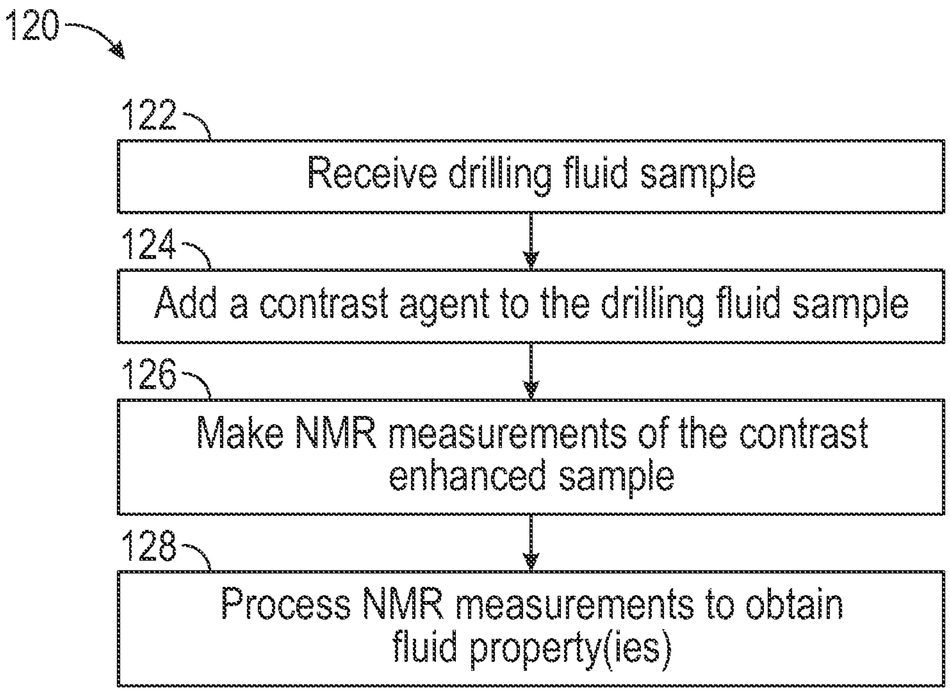
FIG. 2 depicts a flow chart of another disclosed method embodiment.

FIG. 2 depicts a flow chart of similar method embodiment 120 that includes receiving a drilling fluid sample at 122. A contrast agent is added to the sample at 124 to obtain a contrast enhanced sample. NMR measurements are made of the contrast enhanced sample at 126 and processed at 128 to obtain at least one property of the drilling fluid.

With continued reference to FIGS. 1 and 2, it will be appreciated that substantially any suitable drilling fluid may be received at 102, 122. As is known to those of ordinary skill in the art, drilling fluids tend to be highly complex, multi-phase fluids that are commonly subject to non-ambient (e.g., elevated) temperature and/or pressure conditions. Common drilling fluids include emulsions having water and oil phases, with each of the phases including various dissolved components. Common commercial drilling fluids can be water-based (e.g., including a discontinuous oil phase in a continuous water/brine phase) or oil-based (e.g., including discontinuous water/brine phase in a continuous oil or synthetic phase). Drilling fluids further commonly include solids such as clay fillers (and cuttings in used or in-use fluids).

The drilling fluids may be received at substantially any suitable location, for example, in a downhole logging tool or fluid sampling tool, in an in-line NMR sensor, or at a rig site or off-site laboratory. Example measurement configurations are described in more detail below with respect to FIG. 10, however, the disclosed embodiments are not limited in these regards. In example embodiments, the disclosed methods may be used to evaluate pristine (unused) drilling fluid. In other embodiments the disclosed methods may be used to evaluate used (or in service) drilling fluid (e.g., possibly including formation fluids, cuttings, and other materials in addition to the original drilling fluid). Such fluids may be obtained from a drilling rig, for example, from a subterranean wellbore, a mud pit, or elsewhere on the rig. The disclosed embodiments are not limited in these regards.

With further reference to FIGS. 1 and 2, the drilling fluid samples may be modified, for example, by (i) heating or cooling the fluid sample to at least one elevated temperature, (ii) diluting the fluid sample with either an oil-based or water-based dilutant (e.g., an oil-based fluid may be diluted with an oil and a water-based fluid may be diluted with water or brine), and/or (iii) adding a contrast agent to the sample. As noted above, the fluid modification is intended to enhance (increase) a peak separation between oil phase and water phase responses in an NMR measurement, for example, increase the separation between water phase and oil phase peaks in a T1 distribution, a T2 distribution, and/or a T1T2 plot. As described in more detail below with respect to FIGS. 3 and 11, the drilling fluid samples may optionally be filtered prior to modification to remove magnetic debris.

In embodiments in which the fluid sample is heated or cooled, the NMR measurement system may also be heated or cooled such that components of the NMR system (e.g., the permanent magnet(s) and/or the RF antenna) are at substantially the same temperature as the sample, however, the disclosed embodiments are not limited in this regard. In embodiments in which the fluid sample is diluted, the sample may be advantageously diluted using oil or water-based components already present in the fluid.

In certain advantageous embodiments, a contrast agent may be utilized to significantly reduce T1 and/or T2 of the continuous phase in the drilling fluid (e.g., the oil phase for an oil-based fluid) while leaving T1 and T2 of the discontinuous phase largely unchanged. In such embodiments, the contrast agent may be selected to partition preferentially into the continuous phase and may include a magnetic contrast agent dispersed or dissolved in water-based or oil-based fluid. A magnetic contrast agent may include a paramagnetic ion, molecule, or colloid that may be partitioned into either the water phase or oil phase of the fluid. Example magnetic contrast agents include paramagnetic ion complexes including lanthanide or transition metal complexes such as a gadolinium or manganese complexes, transition metal salts including iron, cobalt, manganese, and nickel salts, and magnetic colloids such as ferrofluids. By ferrofluid it is meant a fluid that includes a colloidal suspension of very fine ferromagnetic or ferrimagnetic particles. Particularly suitable ferrofluids may include nanoscale (e.g., less than 100 nm size) iron containing particles such as magnetite or hematite suspended in a fluid such as water or oil.

It will be understood that the contrast agent may be advantageously dispersed or dissolved in a fluid similar to that of the base drilling fluid. In other words, for water-based drilling fluids, the contrast agent may be advantageously dissolved in a water-based liquid (e.g. water or brine). Example contrast agents for water-based drilling fluids may include transition metal salts (e.g., $NiCl_2$) and aqueous ferrofluids. Example contrast agents for oil-based drilling fluids may include an oil-based ferrofluid. In example embodiments a ferrofluid including iron containing magnetic particles coated with a polymer or a surfactant (to promote colloidal stability) may be advantageous. It has been found that in certain drilling fluids, significant peak separation may be achieved using a small amount of the ferrofluid such that the ratio of oil and water in the drilling fluid isn't significantly impacted by the addition of the ferrofluid. For example only, the ferrofluid may make up less than about 1 volume percent of the contrast enhanced or modified fluid sample (e.g., in a range from about 0.01 to about 1 volume percent of the modified sample).

With still further reference to FIGS. 1 and 2, the NMR measurements may be made, for example, as described above. The modified or contrast enhanced fluid sample may be injected (or otherwise inserted) into an NMR measurement tool. A static magnetic field is applied to the sample (e.g., via permanent magnets in the NMR measurement tool). An RF pulse sequence (such as a single CPMG pulse sequence or a set of CPMG sequences) is applied to the sample and NMR signals (echoes) are measured. The NMR signals may be processed, e.g., via inversion, to obtain the NMR measurement, for example, to obtain a T1 distribution, a T2 distribution, and/or a T1T2 plot.

The NMR measurement is further processed to obtain corresponding properties of the fluid, such as an oil water ratio (e.g., a volume ratio) of the sample. For example, the oil water ratio (OWR) may be obtained by evaluating relative and/or absolute amplitudes of oil and water peaks in the NMR measurement. The peaks may further be integrated in one or two dimensions to determine total amplitudes of the peaks (e.g., the area under the peak). In one embodiment the peak amplitudes (or total amplitudes) may be evaluated using an empirical correlation developed by making NMR measurements on a large number of drilling fluid samples and diluted drilling fluid samples having known OWRs. The empirical correlation may include, for example, a mathematical correlation or model between the OWR and peak amplitudes, relative amplitude, and/or total amplitudes of the oil and water peaks in a T1T2 plot or in a T1 and/or T2 distribution.

In certain example embodiments evaluating the NMR measurements may include (i) identifying oil and water peaks in the NMR measurements (e.g., in the T1 distribution, the T2 distribution, and/or the T1T2 plot, (ii) determining an amplitude and/or total amplitude of each of the oil and water peaks, and (iii) correlating the amplitude and/or total amplitudes of the peaks with a mathematical model (e.g., obtained from NMR measurements made on samples having known OWR values) to determine the OWR of the sample.

Figure 3:
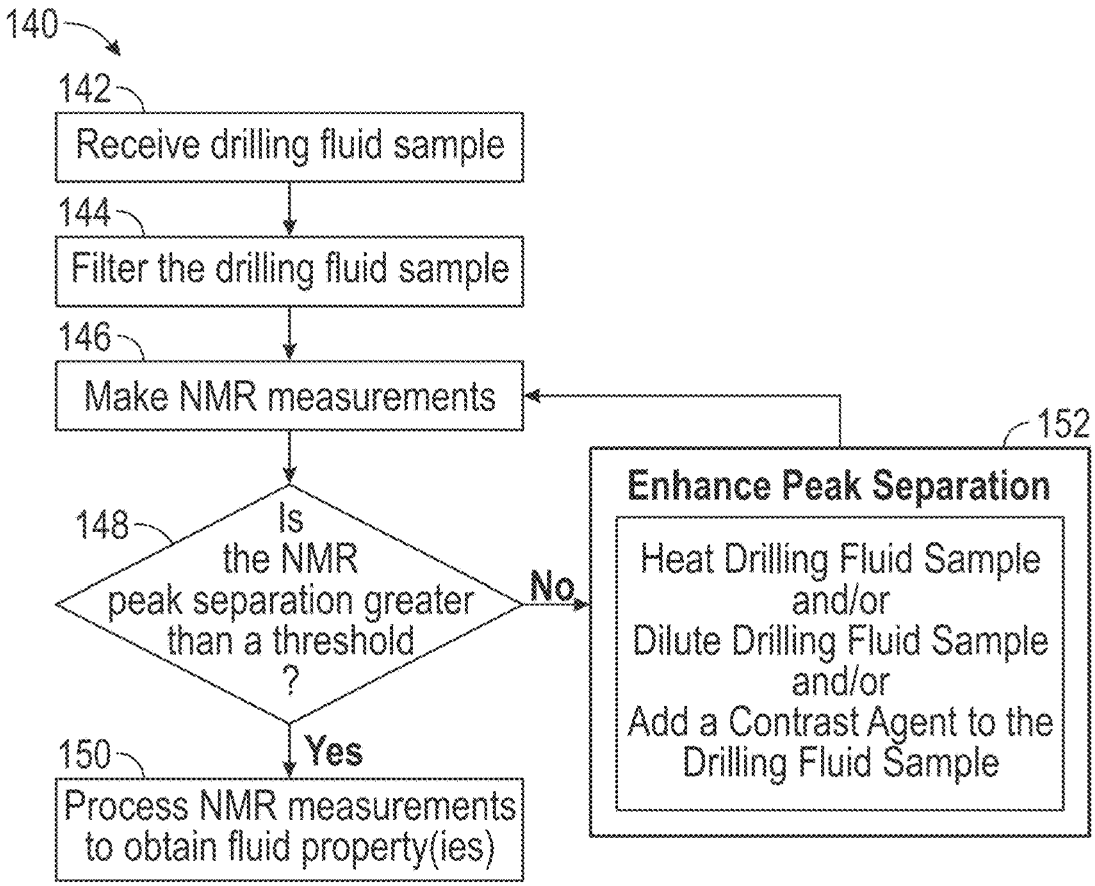
FIG. 3 depicts a flow chart of yet another disclosed method embodiment.

Turning now to FIG. 3 a flow chart of another method embodiment 140 for evaluating drilling fluid is depicted. Method 140 is similar to methods 100 and 120 in that it includes receiving a drilling fluid sample at 142. The sample may be filtered or magnetically filtered to remove particles, magnetic particles, or other debris from the sample, for example, as described in more detail below. NMR measurements of the filtered (or magnetically filtered) sample are made at 146 and evaluated at 148 to determine if the separation between first and second peaks is sufficiently large (e.g., greater than a threshold separation). In certain example embodiments, the peak separation may be sufficiently large (exceeding the threshold) when the difference between the peak T1 values and/or peak T2 values exceeds a threshold. (e.g., in one embodiment such that two distinct peak maxima are observed or in another embodiment such that the peaks are substantially entirely non-overlapping).

With continued reference to FIG. 3, the NMR measurements may be evaluated at 150 to obtain the fluid property(ies) when the peak separation exceeds the threshold. When the peak separation is less than the threshold, it may be enhanced via modifying the sample at 152, for example, via heating or cooling the fluid sample, diluting the fluid sample with a fluid having the same phase as the continuous phase of the drilling fluid, and/or adding a contrast agent to the fluid sample. NMR measurements may be made again at 146 and evaluated at 148 to determine if the peak separation is sufficiently large. It will be appreciated that steps 146, 148, and 152 may be repeated substantially any suitable number of times (e.g., including multiple heating/cooling, dilution, contrast agent additions, or combinations thereof) until the peak separation exceeds the threshold at 148.

Figure 4:
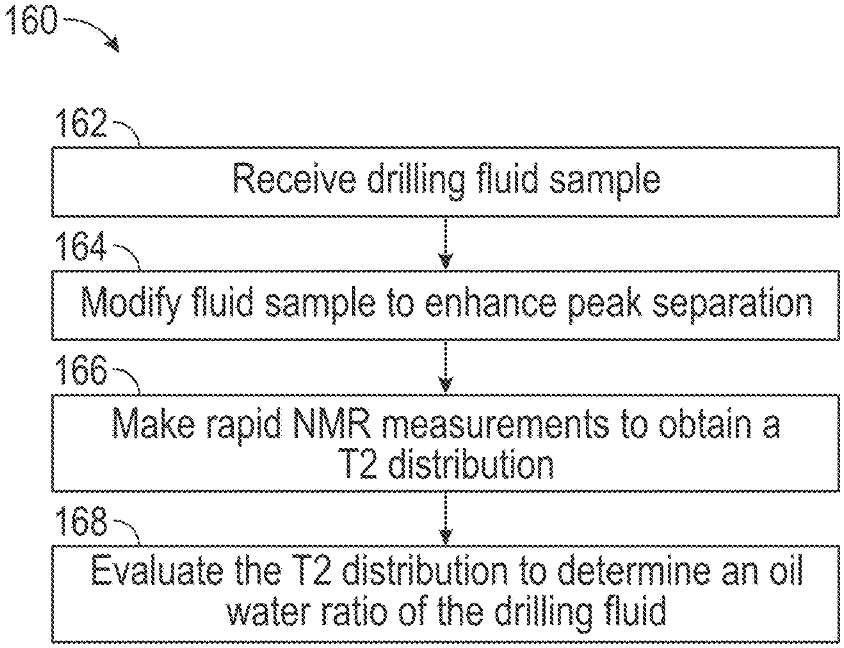
FIG. 4 depicts a flow chart of still another disclosed method embodiment.

Turning now to FIG. 4, a flow chart of a method embodiment 160 for rapidly evaluating drilling fluid is depicted. A sample of the drilling fluid is obtained (or received) at 162 and modified at 164 (e.g., via adding a small volume of a contrast enhancing agent such as ferrofluid) to obtain a modified fluid. Rapid NMR measurements are made of the modified sample at 166 using a CPMG pulse sequence (e.g., a single CPMG pulse sequence) to obtain a T2 distribution. In this example rapid methodology, the measurements do not include obtaining a T1 distribution or a T1T2 plot. Moreover, the inversion-recovery component of the pulse sequence used to generate T1 may be omitted. The T2 distribution is then evaluated at 168 to determine the OWR of the drilling fluid sample (e.g., via correlating the amplitudes or total amplitudes of oil and water peaks in the T2 distribution with a model as described above). The disclosed rapid method may advantageously provide an OWR measurement in several seconds to a few minutes (e.g., 1-3 minutes). Moreover, the disclosed methodology may enable several independent measurements to be made and averaged in a short period of time (e.g., less than 10-15 minutes) to obtain rapid and accurate OWR measurements.

In the examples that follow a number of drilling fluid samples were evaluated using NMR measurements (e.g., as described above using methods 100, 120, 140, and/or 160). All of the disclosed NMR measurements were made using a 4 MHz NMR instrument at the indicated temperature (20 degrees C. if not indicated) and 1 atmosphere pressure. It will be understood, of course, that the disclosed embodiments are not limited to these measurement conditions or to the use of an NMR instrument operating at any particular frequency.

Figure 5A:
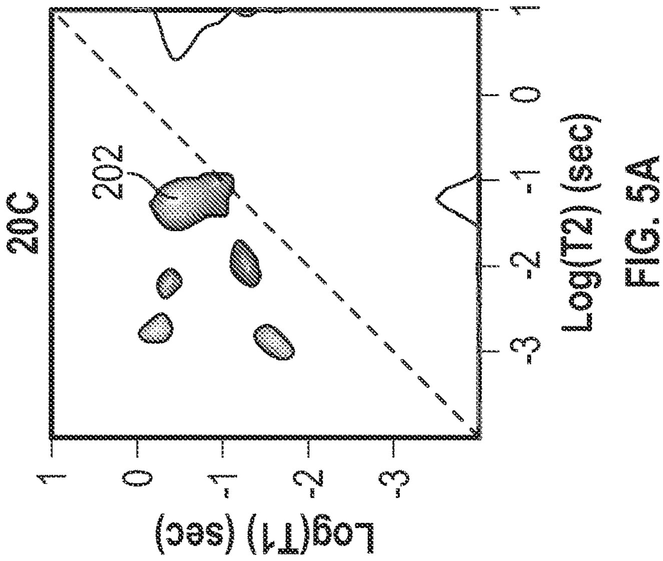
FIGS. 5A, 5B, and 5C (collectively FIG. 5) depict T1T2 plots obtained at temperatures of 20 degrees C. (5A), 40 degrees C. (5B), and 60 degrees C. (5C) for an example drilling fluid.
Figure 5B:
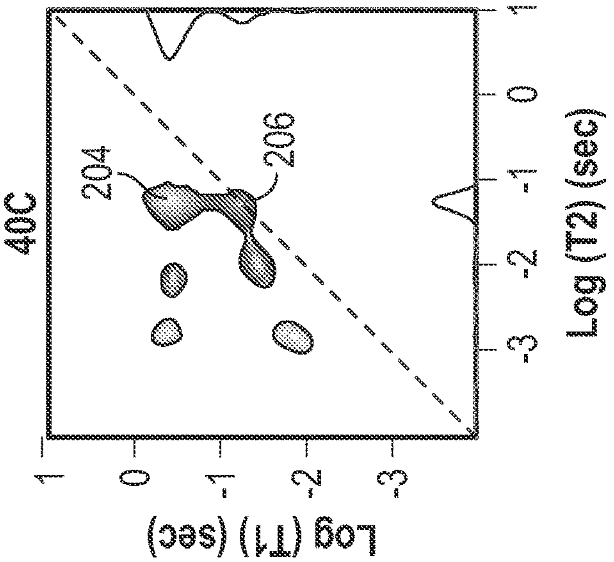
Figure 5C:
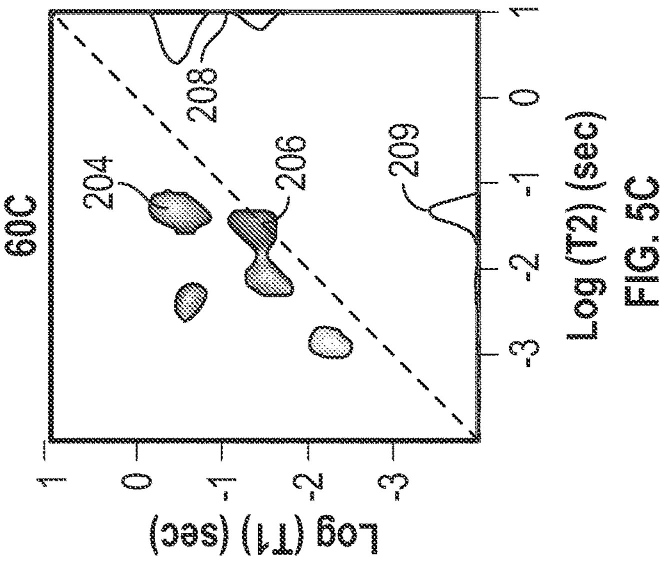

FIGS. 5A, 5B, and 5C (collectively FIG. 5) depict T1T2 plots obtained at temperatures of 20 degrees C. (5A), 40 degrees C. (5B), and 60 degrees C. (5C) for an example drilling fluid. The drilling fluid in this example was synthetic (e.g., an internal olefin) based and had a density of 12.8 pounds per gallon, 23 percent solids, and a 75/25 OWR. The depicted T1T2 plots may be thought of as contour plots that show amplitude in pseudo-color versus T1 on the vertical axis and T2 on the horizontal axis. The T1 and T2 distributions are also shown (in red) on the lower horizontal axis and the right-side vertical axis. In FIG. 5A, a broad amplitude peak is observed at 202 that includes both the oil phase and water phase peaks. In the depicted T1T2 plot there may not be sufficient peak separation to accurately determine the OWR of the fluid (owing to the overlapping oil and water peaks). In FIGS. 5B and 5C heating the sample to 40 degrees C. (5B) and 60 degrees C. (5C) causes a separation of the oil-based peak 204 and the water-based peak 206 (primarily by reducing T1 of the water-based peak). Note that the peaks are fully separated in T1 at 208 but not in T2 at 209. The depicted peak separation in FIGS. 5B and 5C may be sufficient separation for an accurate determination of the OWR of the fluid.

Figure 6A:
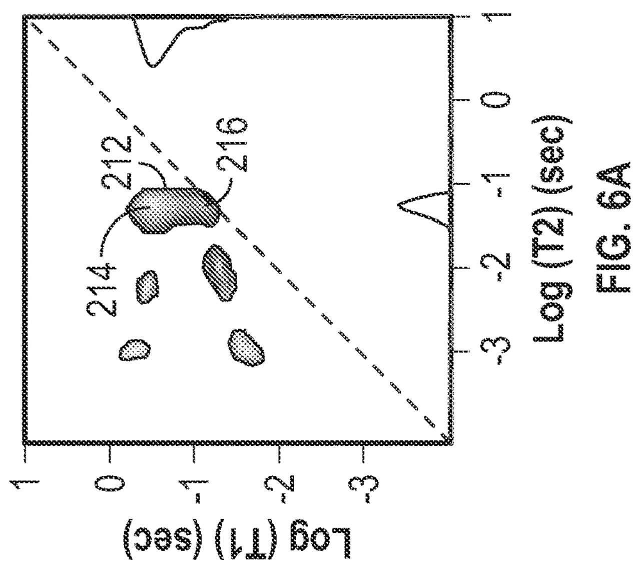
FIGS. 6A, 6B, 6C, 6D, and 6E (collectively FIG. 6) depict T1T2 plots for a drilling fluid sample (6A) and modified samples including incremental additions of a contrast enhancing agent (6B-6E).
Figure 6B:
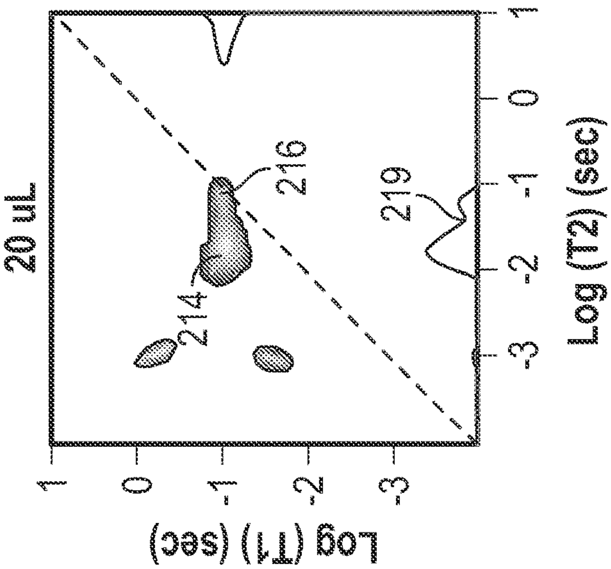
Figure 6C:
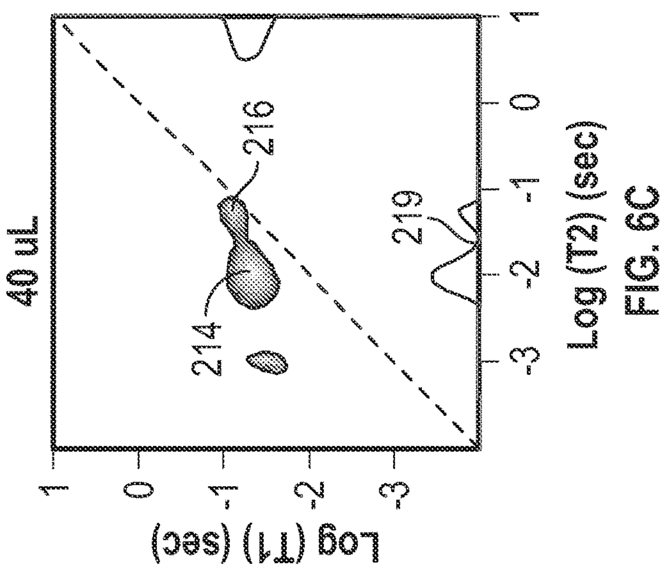
Figure 6E:
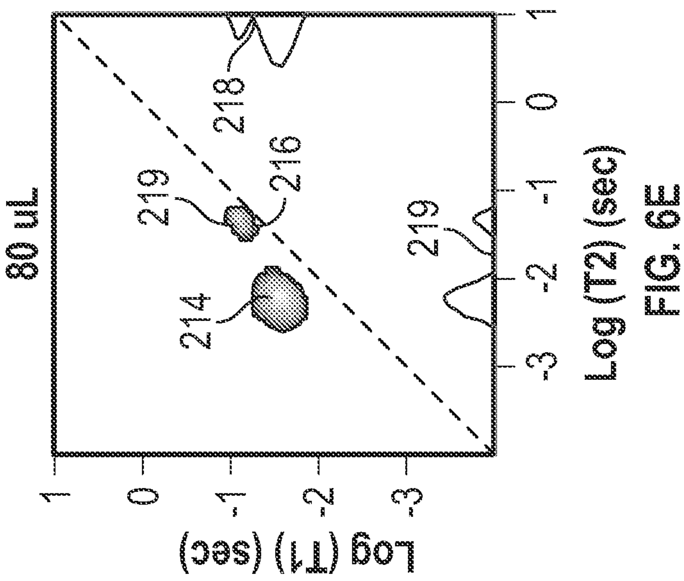
Figure 6D:
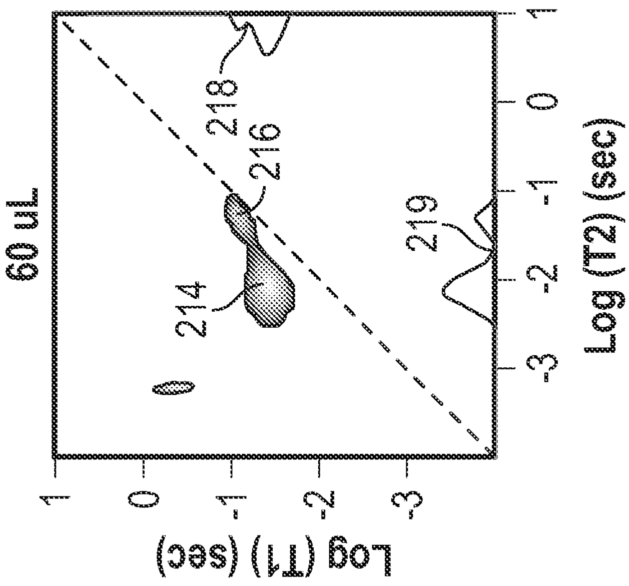

FIGS. 6A, 6B, 6C, 6D, and 6E (collectively FIG. 6) depict T1T2 plots for a drilling fluid sample (6A) obtained from the same fluid type as described above with respect to FIG. 5A and modified samples including incremental additions of a contrast enhancing agent (6B-6E). In this example, a 20 mL sample of the base drilling fluid was obtained. A dilute, oil-based ferrofluid (including nanoscale $Fe_3O_4$ magnetic particles that were colloidally suspended in oil) was added to the base sample at levels of 20 μL (6B), 40 μL (6C), 60 μL (6D), and 80 μL (6E). In FIG. 6A, a single amplitude peak is observed at 212 that includes the overlapping oil phase 214 and water phase 216 peaks. In the depicted T1T2 plot there may not be sufficient peak separation to accurately determine the OWR of the fluid.

In this example, the addition of the ferrofluid to the drilling fluid sample caused the oil phase peak 214 to move down and to the left in the T1T2 plot (to lower T1 and T2 values) while the location of the water peak 216 was substantially unchanged. The change in T1 and T2 relaxation times for the oil phase peak was observed to increase with increasing amounts of added ferrofluid (from 20 μL to 80 μL). In other words a greater change in peak position was observed with increasing amounts of ferrofluid. After the addition of 20 μL of the ferrofluid (6B), the oil phase peak 214 remained somewhat overlapped with the water phase peak 216, however, distinct peaks were clearly observed in T2 at 219 (which may provide for an accurate determination of the OWR of the fluid). Further peak separation was observed after the addition of 40 μL of the ferrofluid (6C) (particularly in T2 where the peaks were fully separated at 219). Still further peak separation was observed after the addition of 60 μL of the ferrofluid (6D) with distinct peaks clearly observed in T1 at 218. Both T1 and T2 peaks were observed to be fully separated after the addition of 80 μL of the ferrofluid (6E).

FIGS. 7A, 7B, 7C, and 7D (collectively FIG. 7) depict T1T2 plots for a freshly prepared drilling fluid sample with and without added ferrofluid (7A and 7B) and an aged sample of the same drilling fluid (aged for 12 hours at 150 degrees C.) with and without added ferrofluid (7C and 7D). The freshly prepared drilling fluid was a clay bearing fluid including 10 percent solids, calcium chloride brine, and a synthetic oil. The OWR of the freshly prepared drilling fluid was 60/40.

Figure 7A:
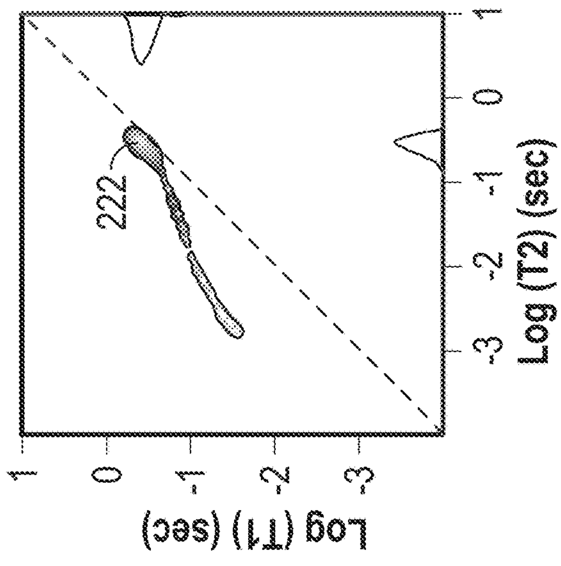
FIGS. 7A, 7B, 7C, and 7D (collectively FIG. 7) depict T1T2 plots for a freshly prepared drilling fluid sample with and without added ferrofluid (7A and 7B) and an aged sample of the same drilling fluid with and without added ferrofluid (7C and 7D).
Figure 7B:
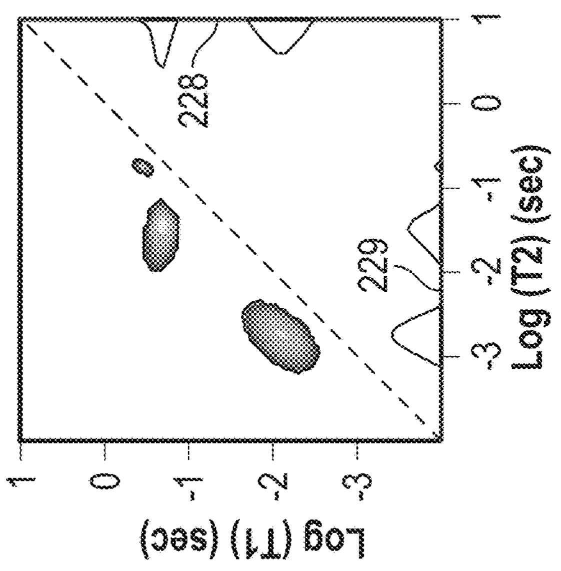
Figure 7C:
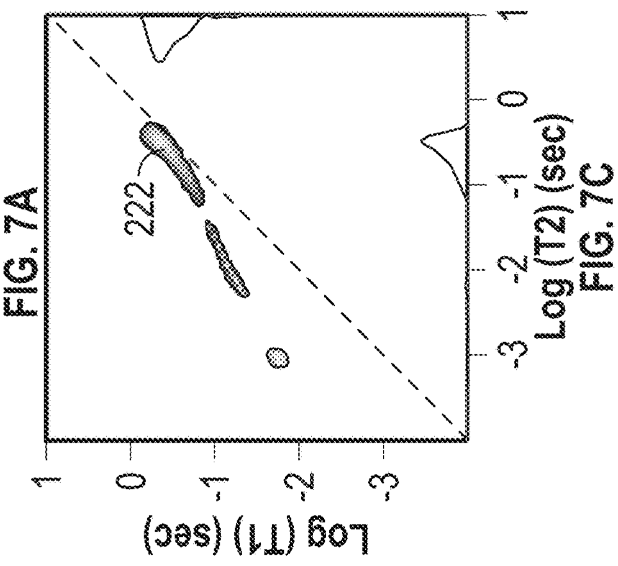
Figure 7D:
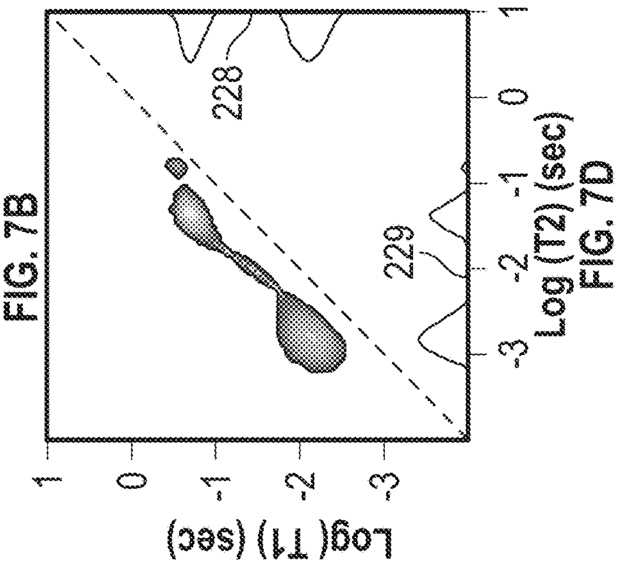

In FIGS. 7A and 7C, amplitude peaks were observed at 222 that included overlapping oil phase and water phase peaks. In the depicted T1T2 plots there may not be sufficient peak separation to accurately determine the OWR of the fluid. In FIGS. 7B and 7D, the freshly made and aged samples were modified by the addition of 20 μl of a concentrated, oil-based ferrofluid (including nanoscale $Fe_3O_4$ magnetic particles that were colloidally suspended in oil) to a 20 mL drilling fluid sample. Significant peak separation was observed for both modified fluids as shown at 228 and 229. The depicted NMR measurements were further evaluated to determine OWRs of 59.2/40.8 and 58.2/41.8 which were in good agreement with the as manufactured value.

FIGS. 8A, 8B, 8C, and 8D (collectively FIG. 8) depict T1T2 plots for first and second drilling fluid field samples with and without added ferrofluid (the first field sample is depicted in 8A and 8B and the second field sample is depicted in 8C and 8D). Both field samples included clay, calcium chloride brine, and a synthetic oil and were obtained after use in a drilling operation. The ferrofluid was identical to that described above in FIG. 7, with the exception that the magnetic particles were suspended in the same synthetic oil used to manufacture the drilling fluid. The field samples were evaluated using a conventional distillation retort methodology to measure corresponding OWRs and densities. The first field sample was found to have an OWR of 74/26 and a density of 14.45 pounds per gallon. The second field sample was found to have an OWR of 67.1/32.9 and a density of 12.65 pounds per gallon.

Figure 8A:
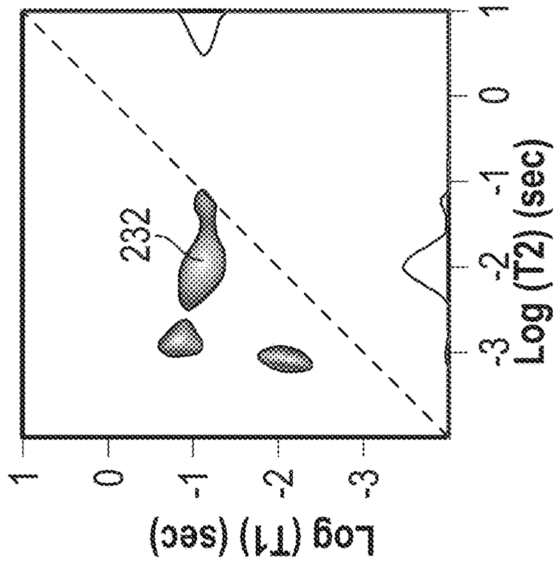
FIGS. 8A, 8B, 8C, and 8D (collectively FIG. 8) depict T1T2 plots for first and second drilling fluid field samples with and without added ferrofluid (the first field sample is depicted in 8A and 8B and the second field sample is depicted in 8C and 8D).
Figure 8B:
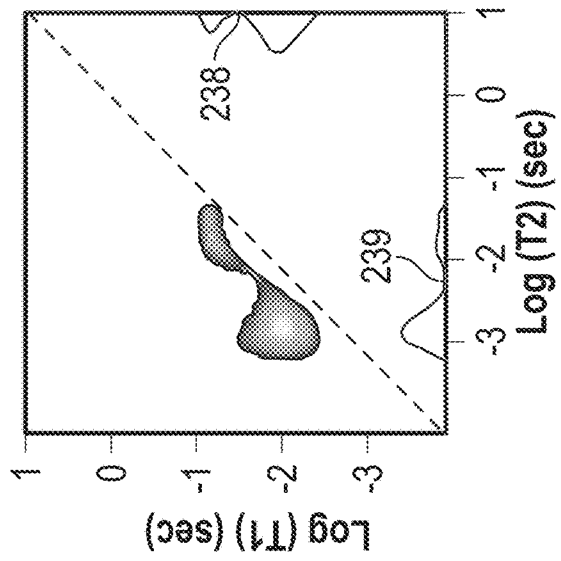
Figure 8C:
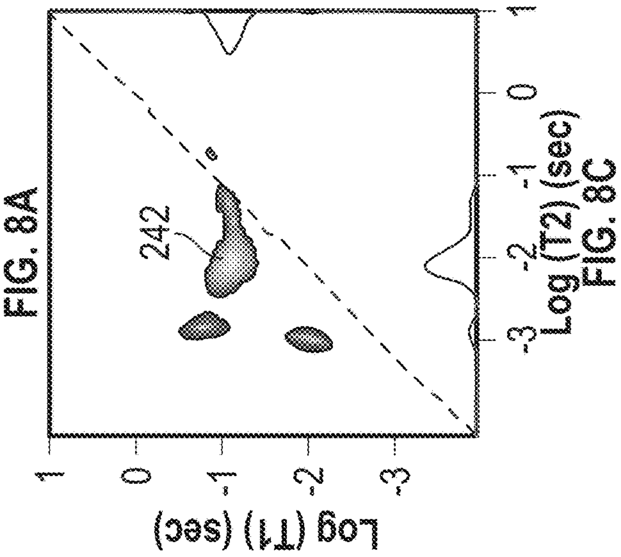
Figure 8D:
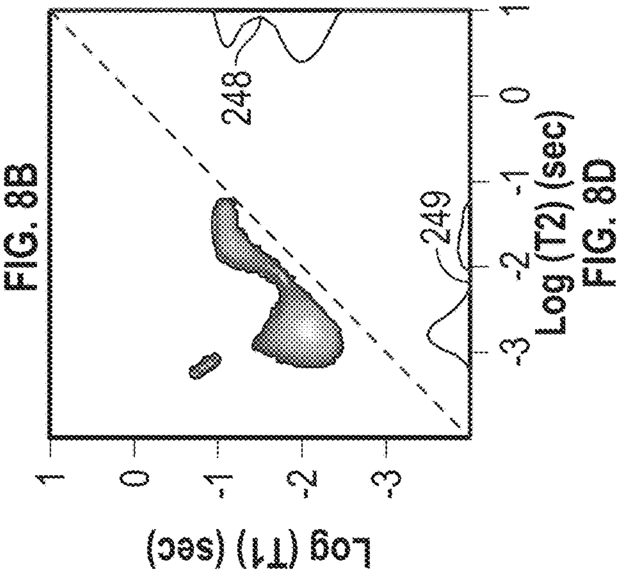

In FIGS. 8A and 8C single amplitude peaks were observed at 232, 242 that included overlapping oil phase and water phase peaks. In the depicted T1T2 plots there may not be sufficient peak separation to accurately determine the OWR of the fluid. In FIGS. 8B and 8D, the first and second field samples were modified by the addition of 20 μL of the above described ferrofluid to a 20 mL drilling fluid sample. Significant peak separation was observed for both modified fluids as shown at 238, 239 and 248, 249. The depicted NMR measurements were further evaluated to determine OWRs of 75.7/24.3 and 68.6/31.2 which were in good agreement with the conventional retort measurements.

Figure 9B:
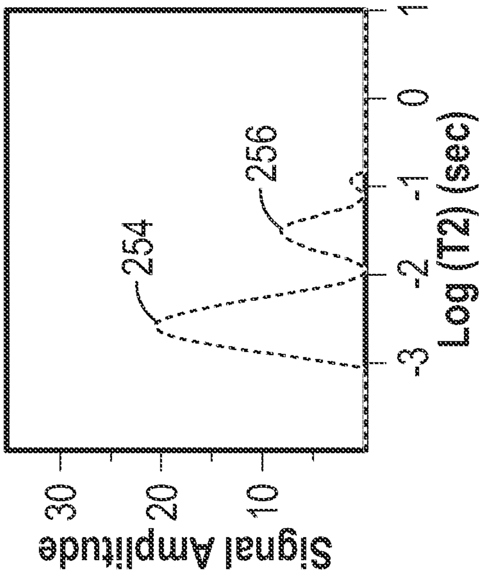
FIGS. 9A, 9B, 9C, and 9D (collectively FIG. 9) depict amplitude versus T2 plots (9A and 9B) and T1T2 plots (9C and 9D) for an example drilling fluid field sample with and without ferrofluid.
Figure 9D:
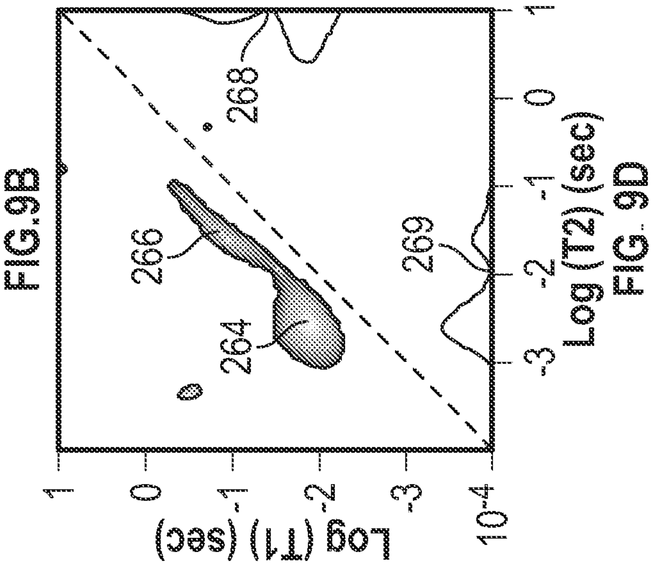
Figure 9A:
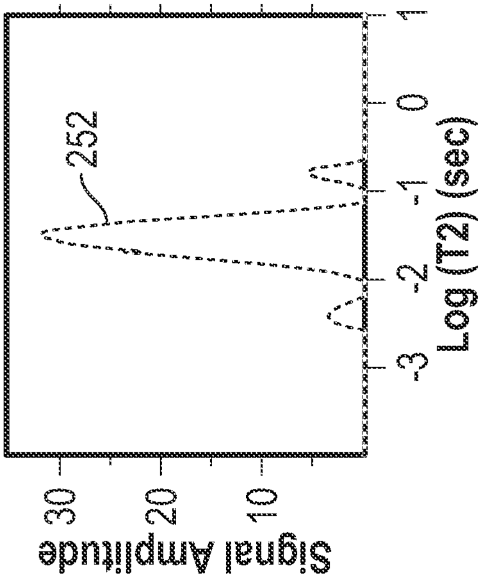
Figure 9C:
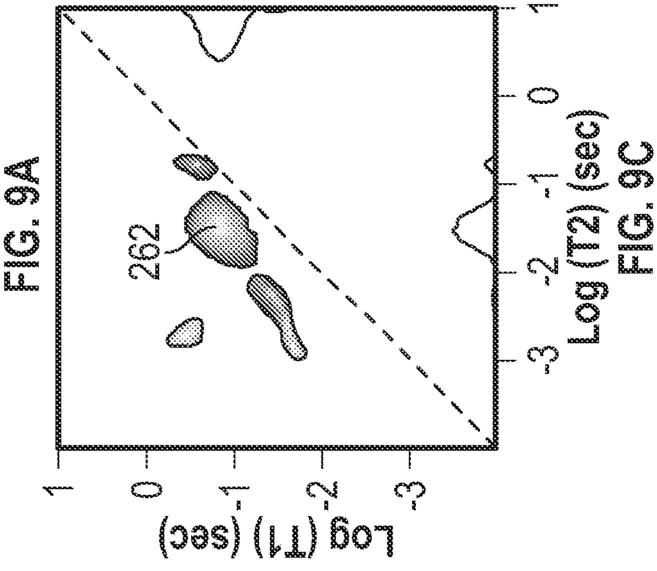

FIGS. 9A, 9B, 9C, and 9D (collectively FIG. 9) depict T2 distributions (9A and 9B) and T1T2 plots (9C and 9D) for a field sample diesel based drilling fluid with and without ferrofluid. FIGS. 9A and 9C depict the T2 distribution and T1T2 plot for the as received sample, while FIGS. 9B and 9D depict the T2 distribution and T1T2 plot after the addition of 20 μL of ferrofluid to a 20 mL of the sample (the ferrofluid was identical to that described above with respect to FIG. 7).

The field sample was evaluated using a conventional distillation retort methodology and was found to have an OWR of 75.1/24.9 and a density of 8.8 pounds per gallon. The T2 distributions (9A and 9B) were obtained using a single CPMG sequence as described above with respect to FIG. 4 (the data acquisition times were about 2 min). The T1T2 plots (9C and 9D) were obtained using the same NMR measurement method as used to obtain the T1T2 plots depicted on FIGS. 5-8 (and had acquisition times of about 25 min).

In FIG. 9A (no ferrofluid), the oil and water peaks overlap in T2 as shown at 252 such that there may be insufficient peak separation to determine OWR. In FIG. 9B (with ferrofluid) distinct oil 254 and water 256 based peaks were observed. These T2 measurements were processed to obtain an OWR of 76.5/23.5. In FIG. 9C (no ferrofluid), the oil and water peaks overlap in the T1T2 plot as shown at 262 such that there may be insufficient peak separation to determine OWR. In FIG. 9D (with ferrofluid) distinct oil 264 and water 266 based peaks were observed. These distinct oil and water peaks were also observed in T1 and T2 as shown at 268 and 269. The data in the T1T2 plot shown on FIG. 9D were processed to obtain an OWR of 76.6/23.4. Note that in this example the rapid T2 methodology (FIG. 4) provided OWR values that were in excellent agreement with the conventional retort methodology and the full NMR (T1T2) methodology.

With reference again to FIGS. 1-4, it will be understood that the depicted method steps, including the fluid sampling, the fluid modifying, the NMR measurements, and the evaluation of the NMR measurements may be performed with full or partial automation or may be performed fully manually. For example, in certain embodiments the fluid samples may be obtained manually, may be manually modified (e.g., via manually adding ferrofluid to the sample), and then manually deployed in an NMR tool for making the NMR measurements. Other embodiments may be partially or full automated. For example only, fluid samples may be automatically obtained from a mud pit, a standpipe, and/or the wellbore, automatically modified (e.g., via injecting a predetermined volume of ferrofluid into the fluid, heating or cooling the fluid to a predetermined temperature, and/or dilution with a reference fluid), and/or automatically making NMR measurements and evaluating the measurements.

Figure 10:
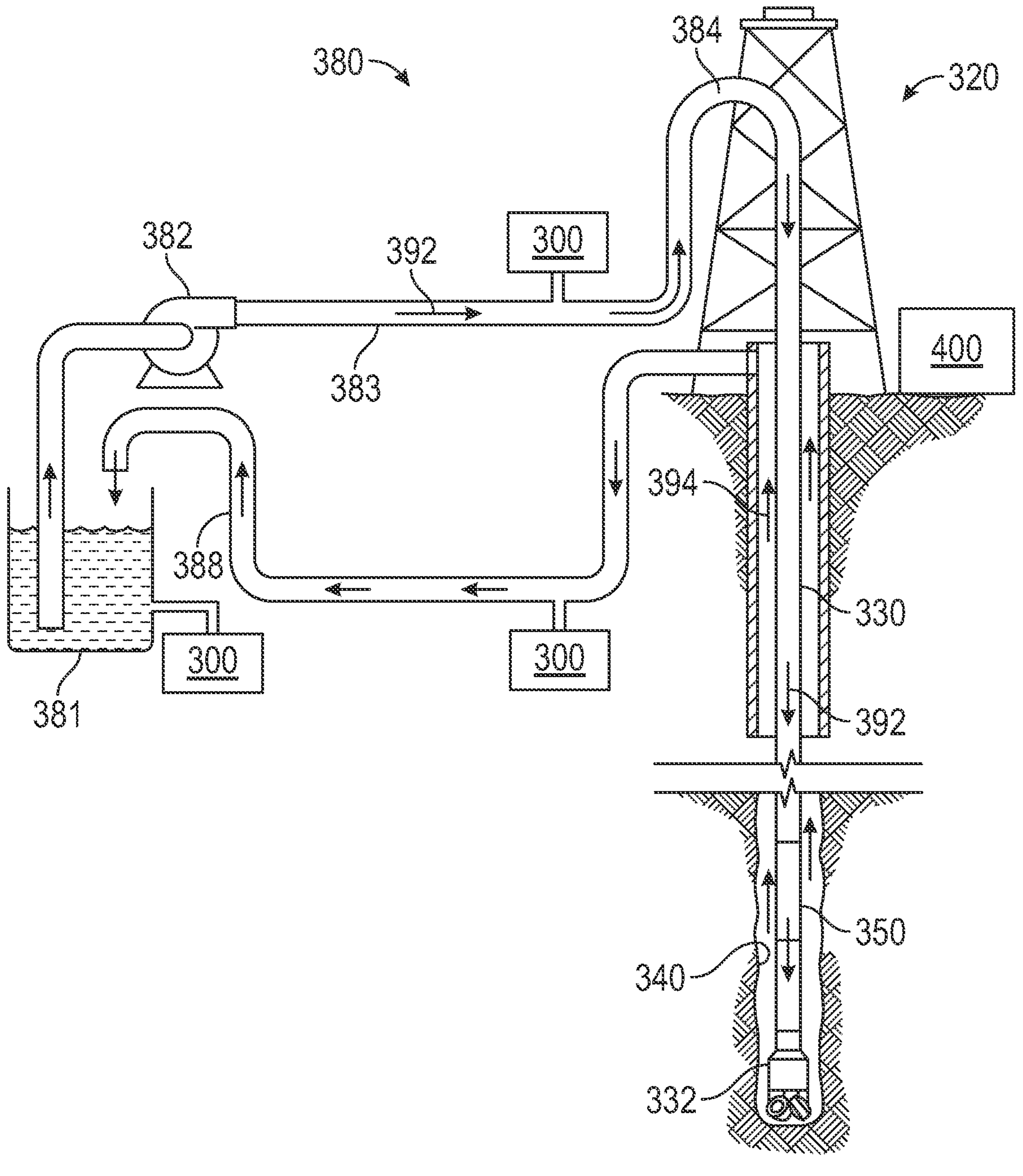
FIG. 10 depicts a drilling rig and surface system including example NMR measurement systems.

FIG. 10 depicts a drilling rig 320 including example NMR measurement systems 300 disclosed herein. The drilling rig 320 may be positioned over a subterranean oil or gas formation (not shown). The rig may include, for example, a derrick and a hoisting apparatus (also not shown) for raising and lowering a drill string 330, which, as shown, extends into wellbore 340 and includes, for example, a drill bit 332 and a downhole fluid sampling and evaluation tool 350.

Drilling rig 320 includes a surface system 380 for controlling the flow of drilling fluid used on the rig (e.g., used in drilling the wellbore 340). In the example embodiment depicted, drilling fluid is pumped downhole (as depicted at 392) via a conventional mud pump 382. The drilling fluid may be pumped, for example, through a standpipe 383 and mud hose 384 in route to the drill string 330. The drilling fluid typically emerges from the drill string 330 at or near the drill bit 332 and creates an upward flow 394 of mud through the wellbore annulus (the annular space between the drill string and the wellbore wall). The drilling fluid then flows through a return conduit 388 to mud pit 381.

As described above, the disclosed system and method embodiments may be advantageously utilized to evaluate drilling fluid in use in a drilling rig (such as rig 320). With continued reference to FIG. 10, surface system 380 may include one or more of the NMR measurement systems 300 (shown schematically) configured for receiving a drilling fluid sample, modifying the sample, making NMR measurements of the modified sample, and evaluating the measurements to determine one or more properties of the drilling fluid. For example only, the NMR measurements system 300 may be deployed in fluid communication with the mud pit 381, the standpipe 392, and/or the return passageway 388 such that fluid samples may be automatically received therefrom. The system may be further configured to automatically modify the fluid samples (e.g., as described above) and to make and evaluate NMR measurements of the modified samples. Other system embodiments may be configured for manual use (or interactive use) with an operator. For example, an operator may instruct the system to obtain and modify the samples and make and evaluate the NMR measurements. Still other system embodiments may be configured to automatically obtain and modify the fluid samples, make the NMR measurements, and then transmit the measurements to a central location for further processing and evaluation. In certain embodiments, an automated system may include hardware configured to sample and modify the drilling fluid (e.g., including a sampling probe or port, tubing, a magnetic filter, a heating element, and/or a syringe) and NMR instrumentation configured to make NMR measurements of modified drill fluid sample. The instrumentation may be further configured, for example to make rheological measurements of the drilling fluid sample either before or after modification. The disclosed embodiments are not limited in regard to the detailed configuration of the system.

With further reference to FIG. 10, drilling rig 320 may further include an NMR testing facility 400 (e.g., a laboratory trailer including an NMR testing apparatus). In manual embodiments, a technician (or other service personnel) may obtain one or more fluid samples for testing. The samples may be transported to the NMR testing facility where they may be modified as described above prior to making and evaluating NMR measurements. The NMR testing facility may further include computing resources for processing and evaluating NMR measurements made by the partially or fully automated measurement system(s) 300.

With still further reference to FIG. 10, drilling rig 320 may further include a downhole formation fluid sampling tool 350 deployed in the drill string 330. While not depicted, the sampling tool may include a port for automatically receiving a sample of the drilling fluid (e.g., from the fluid flowing up the wellbore annulus at 394 and/or from the fluid being pumped down through the drill string at 392). The sampling tool may further be configured to modify the sample (e.g., via injecting a predetermined volume of ferrofluid) and make and evaluate NMR measurements of the modified sample.

With reference again to FIGS. 1-4 and continued reference to FIG. 10 it will be appreciated that receiving the drilling fluid sample in 102, 122, 142, 162 may further include permanently or temporarily removing magnetic material from the drilling fluid prior to modifying the drilling fluid in 104, 124, 144, 164. For example, certain drilling fluids may include iron particulate contamination (e.g., magnetic iron particulate resulting from wear of drill string and other tool components). It may be advantageous to remove such contamination prior to modifying the fluid samples and making the NMR measurements as described above. Magnetic contamination may be removed from the drilling fluid, for example, via deploying one or more permanent magnets or electromagnets in or adjacent to the fluid (or a fluid flow line) to trap or magnetically filter out the magnetic contamination.

Figure 11A:
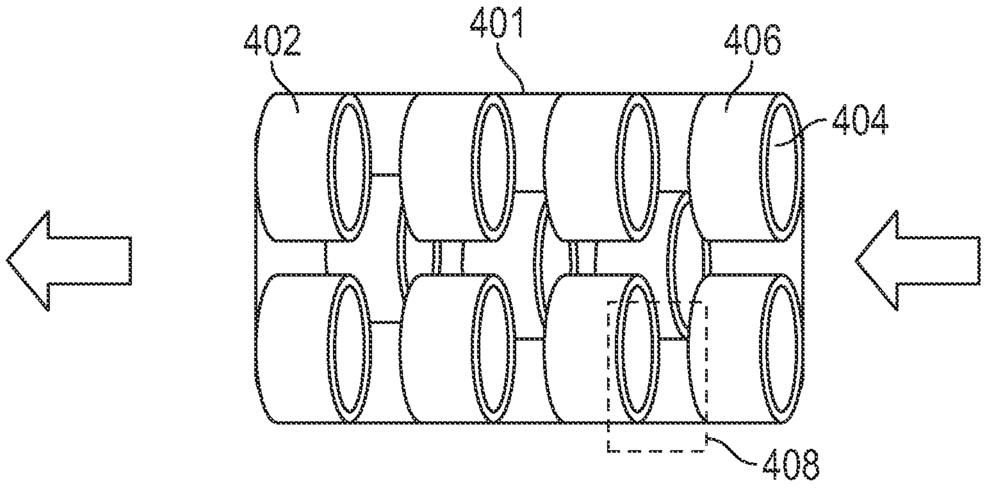
FIGS. 11A and 11B (collectively FIG. 11) depict first and second example configurations for removing magnetic debris from drilling fluid prior to making NMR measurements.
Figure 11B:
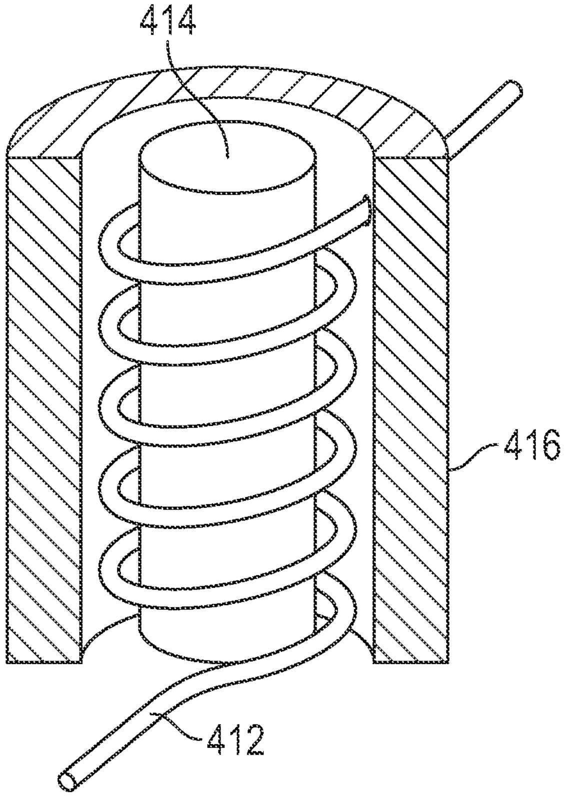

FIGS. 11A and 11B (collectively FIG. 11) depict example configurations for removing magnetic debris from the drilling fluid (or reducing the quantity of magnetic debris in the fluid). In FIG. 11A, permanent magnets 402 having north 404 and south poles 406 are deployed in a fluid flow line 401. The permanent magnets are intended to trap and/or remove magnetic contamination in fluid flowing (as indicated) through the pore space 408 in the flow line 401. In FIG. 11B, a nonmagnetic fluid flow line 412 is deployed about a magnetically permeable rod 414. Application of an electrical current to a 416 coil deployed about the flow line 412 and rod 414 generates a magnetic field that is intended to trap or remove magnetic contamination. Conventional filtration and/or screening may also be employed. Moreover, it will be appreciated that the magnetically removed particles may be added back to the fluid via de-energizing the magnet and reversing the flow direction.

Figure 12:
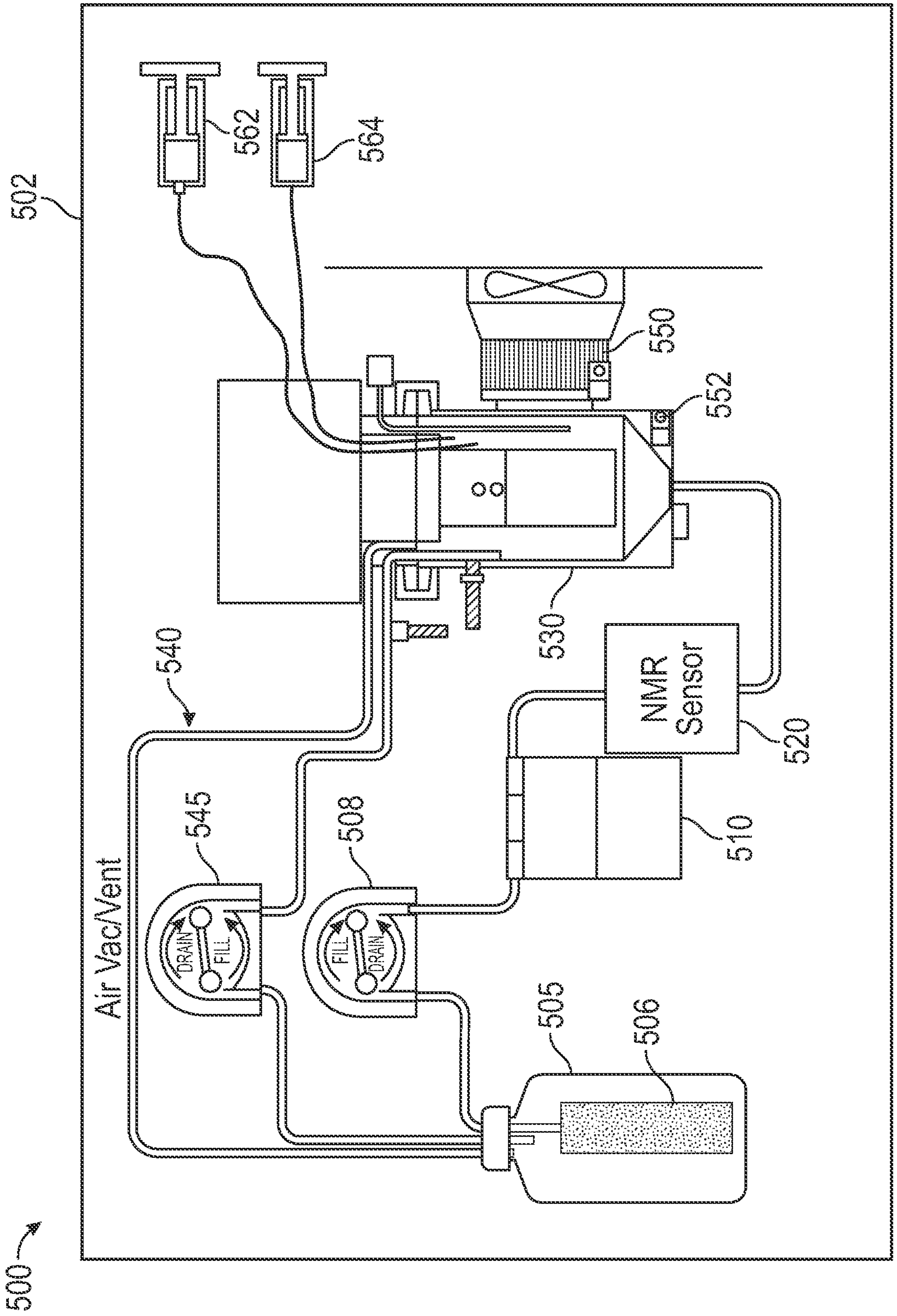
FIG. 12 depicts one example embodiment of a testing apparatus for evaluating drilling fluid.

FIG. 12 depicts one example embodiment of a testing apparatus 500 for evaluating drilling fluid. In the depicted embodiment, the apparatus 500 is configured to make NMR measurements, rheological measurements, and density measurements of the drilling fluid. In certain embodiments, the testing apparatus 500 may be a portable instrument and may be configured for use at substantially any suitable location at a rig site (e.g., in a modular laboratory or adjacent the mud pit or other surface system components).

In the example embodiment depicted, apparatus 500 includes a fluid density measurement cell 510, an NMR measurement cell 520, and a rheology measurement cell 530 deployed in a housing 502. It will be appreciated that the disclosed embodiments are not limited to any particular density measurement cell, NMR measurement cell, and/or rheology measurement cell configurations. A drilling fluid sample may be provided to the instrument in a flask 505 (or other fluid container). The flask 505 may include an internal filter 506 configured to filter the fluid as it is drawn into the instrument measurement cells. Filter 506 may include a conventional filter and/or a magnetic trap as described above with respect to FIG. 11. The filter 506 may also be located external to the flask 505, for example, between the flask 505 and the pump 508.

The fluid sample may be pumped (e.g., via pump 508) from the flask 505 to the density measurement cell 510 where a fluid density measurement may be made. The fluid may then be pumped to the NMR measurement cell 520 where NMR measurements may be made of the un-modified fluid (e.g., prior to modifying the fluid). The fluid may then be pumped (or otherwise transferred) to the rheology measurement cell 530 where rheological measurements (e.g., viscosity) may be made.

With continued reference to FIG. 12, apparatus 500 may be configured to modify the sample of drilling fluid located in the rheology measurement cell 530. For example, the apparatus 500 may further include a temperature control module 550 (including one or more temperature sensors 552) configured to heat and/or cool the fluid in the rheology measurement cell 530. The temperature control module 550 may be configured to control the fluid temperature, for example, in a range from about −10 to about 80 degrees C. (e.g., from about 0 to about 70 degrees C. or from about 5 to about 65 degrees C.). The apparatus 500 may further include one or more metering pumps 562, 564 configured to inject a contrast agent and/or a diluting agent such as oil or brine into the drilling fluid in the rheology measurement cell 530. In the example embodiment depicted, the apparatus 500 includes first and second metering pumps; the first metering pump 562 being configured to inject a dilutant and the second metering pump 564 being configured to inject a contrast agent such as a ferrofluid.

In certain advantageous embodiments, the rheology measurement cell 530 may include a rotational (spin) rheometer. In such embodiments, the modified drilling fluid in cell 530, for example, including any injected dilutants or contrast agents may be blended (e.g., homogenized) via actuation of the rotation elements in the cell 530. The modified drilling fluid sample may then be pumped back to the NMR measurement cell 520 where NMR measurements may be made on the modified fluid sample. The modified drilling fluid may then be expelled from the apparatus 500 or pumped back to the rheology measurement cell 530 for further modification.

With further reference to FIG. 12, apparatus 500 may further include a second (or alternative) fluid inlet/outlet flow channel 540 (including a second pump 545) that bypasses the density measurement cell 510 and NMR measurement cell 520. In the example embodiment depicted, a drilling fluid sample may be pumped directly to the rheology measurement cell 530 via flow channel 540. The fluid in the rheology measurement cell 530 may be modified, for example, as described above and pumped to the NMR measurement cell for NMR evaluation.

While not depicted on FIG. 12, it will be understood that the apparatus 500 may further include an electronic controller configured to control operation of the instrument. For example, such a controller may be configured to instruct the density measurement cell 510, the NMR measurement cell 520, and the rheology measurement cell 530 to make corresponding density, NMR, and rheological measurements on a drilling fluid sample. The controller may be further configured to control the temperature control module 550 and/or the metering pumps 562, 564 as well as inlet pumps 508, 545. In one example embodiment, the controller may be configured to execute one or more of the following steps: (i) instruct pump 508 to transfer a drilling fluid sample to the density measurement cell 510, (ii) instruct the density measurement cell 510 to make a density measurement, (iii) instruct pump 508 to transfer the drilling fluid sample to the NMR measurement cell 520, (iv) instruct the NMR measurement cell 520 to make an NMR measurement, (v) evaluate the NMR measurement for a peak separation, (vi) instruct pump 508 to transfer the fluid sample to the rheology measurement cell 530, (vii) instruct the rheology measurement cell to make rheology measurements, (viii) instruct the temperature control module 550 and/or the metering pump 562, 564 to modify the drilling fluid sample (e.g., when the NMR peak separation is less than a threshold), (ix) instruct pump 508 to transfer the modified fluid sample to the NMR measurement cell 520, and (x) instruct the NMR measurement cell 520 to make an NMR measurement of the modified fluid sample.

It will be understood that the disclosure includes numerous embodiments. These embodiments include, but are not limited to, the following embodiments.

In a first embodiment, a method for evaluating a multiphase drilling fluid includes (a) receiving a sample of the multiphase drilling fluid; (b) modifying the sample to enhance a separation of a first NMR peak corresponding to a first fluid phase component and a second NMR peak corresponding to a second fluid phase component; (c) causing a nuclear magnetic resonance (NMR) instrument to make an NMR measurement of the modified sample; and (d) processing the NMR measurement to compute a property of the drilling fluid.

A second embodiment includes the first embodiment wherein the sample of drilling fluid is received from a surface system of a drilling rig.

A third embodiment includes any one of the first through second embodiments, wherein modifying the sample in (b) comprises heating the sample to at least one elevated temperature or cooling the sample to a lower temperature.

A fourth embodiment includes any one of the first through third embodiments, wherein modifying the sample in (b) comprises diluting the sample.

A fifth embodiment includes any one of the first through fourth embodiments, wherein modifying the sample in (b) comprises adding a contrast agent to the sample, the contrast agent partitioning preferentially into a continuous phase of the sample.

A sixth embodiment includes the fifth embodiment, wherein the contrast agent comprises at least one of a paramagnetic ion complex, a transition metal complex, a transition metal salt, and a magnetic colloid.

A seventh embodiment includes the sixth embodiment, wherein the contrast agent is a ferrofluid comprising nanoscale, iron containing magnetic particles colloidally suspended in an oil-based or water-based fluid.

An eighth embodiment includes the seventh embodiment, wherein a concentration of the ferrofluid in the modified sample is in a range from about 0.01 to about 1 volume percent.

A ninth embodiment includes any one of the first through eighth embodiments, wherein the NMR measurements comprise at least one of a T1 distribution, a T2 distribution, and a T1T2 plot.

A tenth embodiment includes the ninth embodiment, wherein the first NMR peak and the second NMR peak comprise first and second amplitude peaks in at least one of the T1 distribution, the T2 distribution, and the T1T2 plot.

An eleventh embodiment includes any one of the first through tenth embodiments, wherein the property of the drilling fluid comprises an oil water ratio.

A twelfth embodiment includes the eleventh embodiment, wherein (d) further comprises: identifying oil and water peaks in the NMR measurements; determining an amplitude for each of the identified peaks; and processing the determined amplitudes with a model that correlates the determined amplitudes with the oil water ratio.

A thirteenth embodiment includes any one of the first through twelfth embodiments, wherein (c) further comprises: applying a static magnetic field to the modified sample; applying a set of Carr-Purcell-Meiboom-Gill pulse sequences to the modified sample; measuring echoes corresponding to the applied pulse sequences; and inverting the echoes to obtain a T1T2 plot.

A fourteenth embodiment includes any one of the first through thirteenth embodiments, wherein: the NMR instrument applies a Carr-Purcell-Meiboom-Gill pulse sequence to the modified sample in (c) to obtain a T2 distribution; the NMR measurement is not a T1 distribution or a T1T2 plot; and the T2 distribution is processed in (d) to compute an oil water ratio of the drilling fluid.

A fifteenth embodiment includes any one of the first through fourteenth embodiments, wherein receiving the sample in (a) comprises receiving the sample of the multiphase drilling fluid and magnetically filtering the received sample prior to modifying the sample in (b).

In a sixteenth embodiment a method for evaluating drilling fluid includes (a) receiving a sample of the drilling fluid, the sample including a water phase and an oil phase; (b) causing a nuclear magnetic resonance (NMR) instrument to make an NMR measurement received sample; (c) evaluating a peak separation between a first NMR peak and a second NMR peak, the first NMR peak corresponding to the water phase and the second NMR peak corresponding to the oil phase; (d) modifying the sample to enhance the peak separation when the peak separation in (c) is less than a threshold; and (e) processing the NMR measurement to compute a property of the drilling fluid when the peak separation in (c) is greater than the threshold.

A seventeenth embodiment includes the sixteenth embodiment and further comprises repeating (c) and (d) until the peak separation is greater than the threshold.

An eighteenth embodiment includes any one of the sixteenth through seventeenth embodiments, wherein modifying the sample in (d) comprises at least one of heating or cooling the sample, diluting the sample, and adding a contrast agent to the sample, the contrast agent partitioning preferentially into a continuous phase of the sample.

A nineteenth embodiment includes the eighteenth embodiment, wherein the contrast agent is a ferrofluid comprising nanoscale, iron containing magnetic particles colloidally suspended in an oil-based or water-based fluid.

A twentieth embodiment includes any one of the sixteenth through the nineteenth embodiments, wherein: the NMR measurements comprise at least one of a T1 distribution, a T2 distribution, and a T1T2 plot; and (e) further comprises identifying oil and water peaks in the NMR measurements, determining an amplitude for each of the identified peaks, and processing the determined amplitudes with a model that correlates the amplitudes with an oil water ratio of the sample.

A twenty-first embodiment includes any one of the sixteenth through the twentieth embodiments, wherein the NMR instrument applies a Carr-Purcell-Meiboom-Gill pulse sequence to the modified sample to obtain a T2 distribution; the NMR measurement is not a T1 distribution or a T1T2 plot; and the T2 distribution is processed to compute an oil water ratio of the drilling fluid.

In a twenty-second embodiment a system for evaluating a multiphase drilling fluid includes a port configured for receiving the drilling fluid; hardware configured to modify the received drilling fluid; an NMR instrument configured to make NMR measurements on the modified drilling fluid; and a processor configured to process the NMR measurements to compute at least one property of the drilling fluid.

A twenty-third embodiment includes the twenty-second embodiment, wherein the system is configured to automatically receive the drilling fluid, modify the received drilling fluid, make the NMR measurements on the modified drilling fluid, and compute the at least one property of the drilling fluid.

In a twenty-fourth embodiment an apparatus for evaluating a multiphase drilling fluid includes a fluid inlet channel configured to receive a drilling fluid sample; a density measurement cell in fluid communication with the fluid inlet channel and configured to make a density measurement of the drilling fluid sample; an NMR measurement cell in fluid communication with the fluid inlet channel and configured to make an NMR measurement of the drilling fluid sample; a rheology measurement cell in fluid communication with the fluid inlet channel and configured to make a rheology measurement of the drilling fluid sample; a temperature control module configured to control a temperature of the drilling fluid sample in the rheology measurement cell; and a metering pump configured to inject a modifying agent into the rheology measurement cell to modify the drilling fluid sample.

A twenty-fifth embodiment includes the twenty-fourth embodiment, wherein the fluid inlet channel comprises a pump configured to transfer the drilling fluid sample between the density measurement cell, the NMR measurement cell, and the rheology measurement cell.

A twenty-sixth embodiment includes the twenty-fifth embodiment, further comprising an electronic controller configured to cause the pump to transfer the drilling fluid sample to the rheology measurement cell; cause the temperature control module or the metering pump to modify the drilling fluid sample; cause the pump to transfer the modified drilling fluid sample to the NMR measurement cell; and cause the NMR measurement cell to make an NMR measurement of the modified drilling fluid sample.

Although NMR characterization of modified drilling fluids has been described in detail, it should be understood that various changes, substitutions and alterations can be made herein without departing from the spirit and scope of the disclosure as defined by the appended claims.

What is claimed is:

1. A method for evaluating a multiphase drilling fluid, the method comprising (a) receiving a sample of the multiphase drilling fluid;

(b) modifying the sample to enhance a separation of a first NMR peak corresponding to a first fluid phase component and a second NMR peak corresponding to a second fluid phase component;

(c) causing a nuclear magnetic resonance (NMR) instrument to make an NMR measurement of the modified sample; and (d) processing the NMR measurement to compute a property of the multiphase drilling fluid.

2. A method for evaluating drilling fluid, the method comprising:

(a) receiving a sample of the drilling fluid, the sample including a water phase and an oil phase;

(b) causing a nuclear magnetic resonance (NMR) instrument to make an NMR measurement of the received sample;

(c) evaluating a peak separation between a first NMR peak and a second NMR peak, the first NMR peak corresponding to the water phase and the second NMR peak corresponding to the oil phase;

(d) modifying the sample to enhance the peak separation when the peak separation in (c) is less than a threshold; and (e) processing the NMR measurement to compute a property of the drilling fluid when the peak separation in (c) is greater than the threshold.

3. A system for evaluating a multiphase drilling fluid, the system comprising:

a port configured for receiving the drilling fluid;

hardware configured to modify the received drilling fluid;

an NMR instrument configured to make NMR measurements on the modified drilling fluid; and a processor configured to process the NMR measurements to compute at least one property of the drilling fluid.

4. An apparatus for evaluating a multiphase drilling fluid, the apparatus comprising:

a fluid inlet channel configured to receive a drilling fluid sample;

a density measurement cell in fluid communication with the fluid inlet channel and configured to make a density measurement of the drilling fluid sample;

an NMR measurement cell in fluid communication with the fluid inlet channel and configured to make an NMR measurement of the drilling fluid sample;

a rheology measurement cell in fluid communication with the fluid inlet channel and configured to make a rheology measurement of the drilling fluid sample;

a temperature control module configured to control a temperature of the drilling fluid sample in the rheology measurement cell; and a metering pump configured to inject a modifying agent into the rheology measurement cell to modify the drilling fluid sample.

5. The method of claim 1, wherein receiving the sample in (a) comprises receiving the sample of the multiphase drilling fluid and magnetically filtering the received sample prior to modifying the sample in (b).

6. The method of claim 1, wherein the sample of drilling fluid is received from a surface system of a drilling rig.

7. The method of claim 1, wherein modifying the sample in (b) comprises heating the sample to at least one elevated temperature or cooling the sample to a lower temperature.

8. The method of claim 1, wherein modifying the sample in (b) comprises diluting the sample.

9. The method of claim 1, wherein modifying the sample in (b) comprises adding a contrast agent to the sample, the contrast agent partitioning preferentially into a continuous phase of the sample.

10. The method of claim 1, wherein the NMR measurement comprises at least one of a T1 distribution, a T2 distribution, and a T1T2 plot.

11. The method of claim 1, wherein the property of the multiphase drilling fluid comprises an oil water ratio.

12. The method of claim 1, wherein (c) further comprises:

(c1) applying a static magnetic field to the modified sample;

(c2) applying a set of Carr-Purcell-Meiboom-Gill pulse sequences to the modified sample;

(c3) measuring echoes corresponding to the applied pulse sequences; and (c4) inverting the echoes to obtain a T1T2 plot.

13. The method of claim 1, wherein:

the NMR instrument applies a Carr-Purcell-Meiboom-Gill pulse sequence to the modified sample in (c) to obtain a T2 distribution;

the NMR measurement is not a T1 distribution or a T1T2 plot; and the T2 distribution is processed in (d) to compute an oil water ratio of the drilling fluid.

14. The method of claim 2, further comprising:

repeating (c) and (d) until the peak separation is greater than the threshold.

15. The method of claim 2, wherein modifying the sample in (d) comprises at least one of heating or cooling the sample, diluting the sample, and adding a contrast agent to the sample, the contrast agent partitioning preferentially into a continuous phase of the sample.

16. The method of claim 2, wherein the NMR measurement comprises at least one of a T1 distribution, a T2 distribution, and a T1T2 plot; and (e) further comprises identifying oil and water peaks in the NMR measurement, determining an amplitude for each of the identified peaks, and processing the determined amplitudes with a model that correlates the amplitudes with an oil water ratio of the sample.

17. The method of claim 2, wherein:

the NMR instrument applies a Carr-Purcell-Meiboom-Gill pulse sequence to the modified sample to obtain a T2 distribution;

the NMR measurement is not a T1 distribution or a T1T2 plot; and the T2 distribution is processed to compute an oil water ratio of the drilling fluid.

18. The system of claim 3, wherein the system is configured to automatically receive the drilling fluid, modify the received drilling fluid, make the NMR measurements on the modified drilling fluid, and compute the at least one property of the drilling fluid.

19. The apparatus of claim 4, wherein the fluid inlet channel comprises a pump configured to transfer the drilling fluid sample between the density measurement cell, the NMR measurement cell, and the rheology measurement cell.

20. The method of claim 9, wherein the contrast agent comprises at least one of a paramagnetic ion complex, a transition metal complex, a transition metal salt, and a magnetic colloid.

21. The method of claim 10, wherein the first NMR peak and the second NMR peak comprise a first amplitude peak and a second amplitude peak in at least one of the T1 distribution, the T2 distribution, and the T1T2 plot.

22. The method of claim 11, wherein (d) further comprises:

identifying oil and water peaks in the NMR measurement;

determining an amplitude for each of the identified peaks; and processing the determined amplitudes with a model that correlates the determined amplitudes with the oil water ratio.

23. The method of claim 15, wherein the contrast agent is a ferrofluid comprising nanoscale, iron containing magnetic particles colloidally suspended in an oil-based or water-based fluid.

24. The apparatus of claim 19, further comprising an electronic controller configured to:

cause the pump to transfer the drilling fluid sample to the rheology measurement cell;

cause the temperature control module or the metering pump to modify the drilling fluid sample;

cause the pump to transfer the modified drilling fluid sample to the NMR measurement cell; and cause the NMR measurement cell to make an NMR measurement of the modified drilling fluid sample.

25. The method of claim 20, wherein the contrast agent is a ferrofluid comprising nanoscale, iron containing magnetic particles colloidally suspended in an oil-based or water-based fluid.

26. The method of claim 25, wherein a concentration of the ferrofluid in the modified sample is in a range from about 0.01 to about 1 volume percent.

* * * * *